(12) United States Patent
Tsen et al.

(10) Patent No.: US 6,251,607 B1
(45) Date of Patent: Jun. 26, 2001

(54) **PCR PRIMERS FOR THE RAPID AND SPECIFIC DETECTION OF *SALMONELLA TYPHIMURIUM***

(75) Inventors: Hau-Yang Tsen; Jer-Sheng Lin, both of Taichung (TW)

(73) Assignee: National Science Council of Republic of China, Taipei (TW)

( * ) Notice: Subject to any disclaimer, the term of this patent is extended or adjusted under 35 U.S.C. 154(b) by 0 days.

(21) Appl. No.: 09/457,474

(22) Filed: Dec. 9, 1999

(51) Int. Cl.[7] .............................. C12Q 1/68; C12P 19/34; C07H 21/04
(52) U.S. Cl. ........................... 435/6; 435/91.2; 536/23.2; 536/23.7; 536/24.32; 536/24.33
(58) Field of Search ..................... 435/6, 91.2; 536/23.2, 536/23.7, 24.32, 24.33

(56) References Cited

PUBLICATIONS

Lu, C.–D. and Abdelal, A.T. Gene 123:143–144, 1993.*
Erlich, H.A. et al. Science 252:1643–1651, Jun. 1991.*
Boyd, E.F. et al. Proc. Natl. Acad. Sci. USA 91:1280–1284, Feb. 1994.*

Zwadyk, P. Zinsser Microbiology, 20th ed., Joklik, W.K. et al, eds., Appleton & Lange, Norwalk, 1992, Chapter 35, p. 556–565.*

* cited by examiner

*Primary Examiner*—Carla J. Myers
*Assistant Examiner*—Diana Johannsen
(74) *Attorney, Agent, or Firm*—Bacon & Thomas

(57) ABSTRACT

The invention provides a set of two PCR primers designed based on a DNA sequence of a gene encoding malic acid dehydrogenase and a specific DNA of *Salmonella typhimurium*. The invention provides also a DNA probe specific for the above-mentioned PCR primers. Finally, a PCR method using above-mentioned primers is provided for the rapid and specific detection of *Salmonella typhimurium* in food and clinical specimens such as human fecal specimens. Said PCR method comprises further a Southern hybridization assay for detecting PCR products. The whole process could be shortened from 5–7 days for BAM method to 1–2 days.

3 Claims, 6 Drawing Sheets

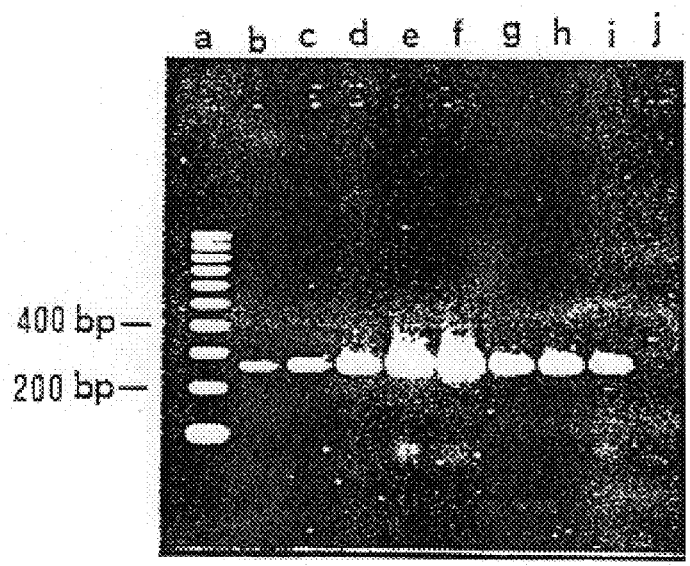
*Fig.* 1 (A)
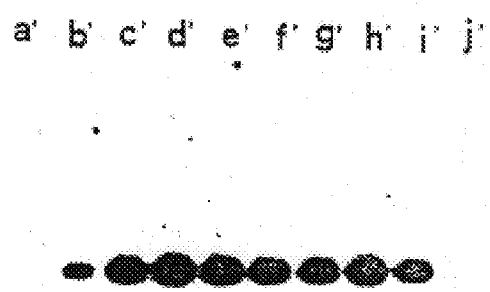
*Fig.* 1 (B)

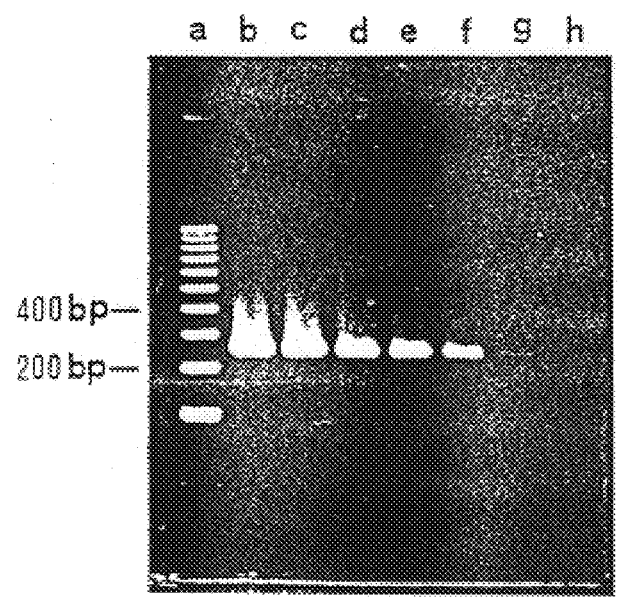
*Fig.* 3 (A)
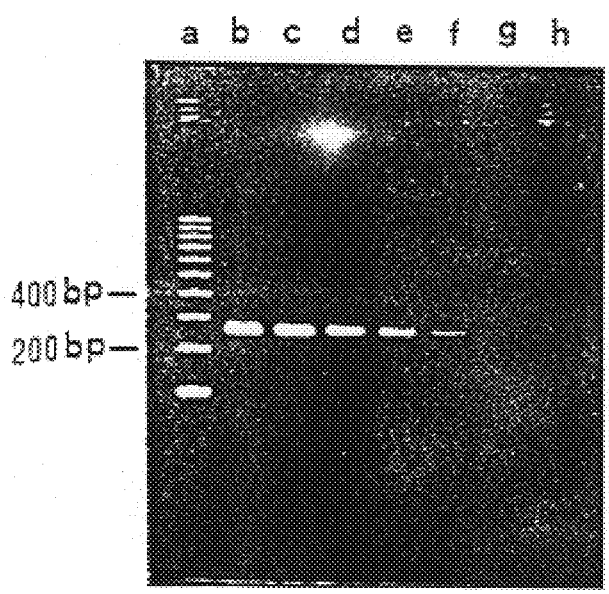
*Fig.* 3 (B)

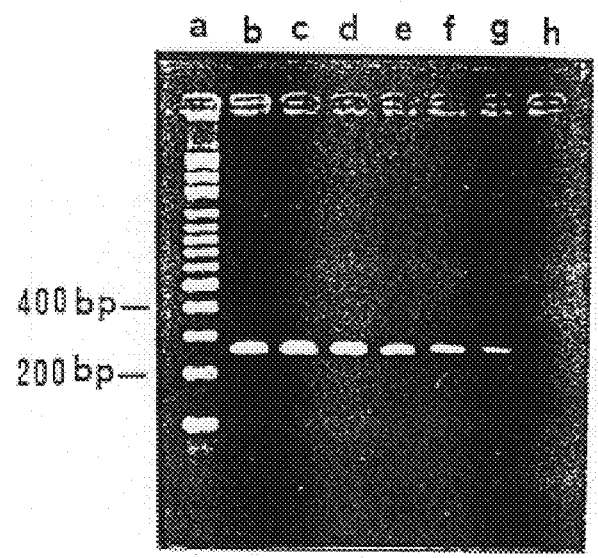
*Fig.* 4 (A)
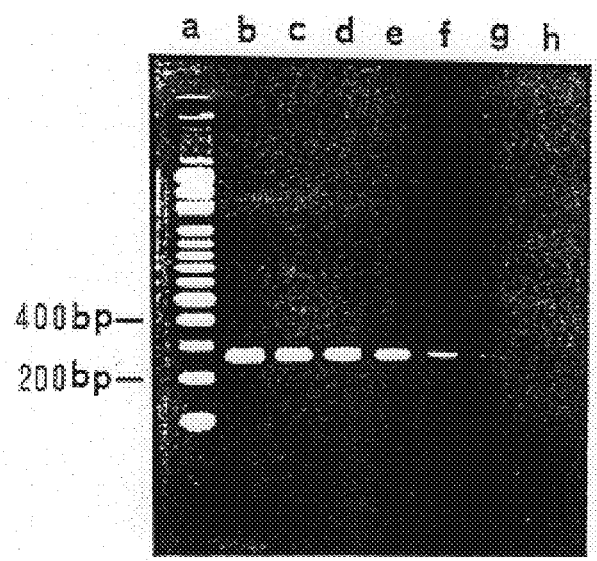
*Fig.* 4 (B)

SEQUENCE LISTING

```
<160> NUMBER OF SEQ ID NOS: 3

<210> SEQ ID NO: 1
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 1
tgccaacgga agttgaagtg                                              20

<210> SEQ ID NO: 2
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 2
cgcattccac cacgcccttc                                              20
```

-continued

```
<210> SEQ ID NO: 3
<211> LENGTH: 21
<212> TYPE: DNA
<213> ORGANISM: Artificial Sequence
<220> FEATURE:
<223> OTHER INFORMATION: Description of Artificial Sequence: probe

<400> SEQUENCE: 3
gtcgcagatt ccaggcgtaa g                                           21
```

PCR PRIMERS FOR THE RAPID AND SPECIFIC DETECTION OF *SALMONELLA TYPHIMURIUM*

BACKGROUND OF THE INVENTION

1. Field of the Invention

The invention relates to PCR primers designed based on a DNA sequence of a gene encoding malic acid dehydrogenase and a specific DNA of *Salmonella typhimurium*, to a probe used in PCR, and to a PCR method for the rapid and specific detection of *Salmonella typhimurium* in food and clinical specimens.

2. Description of related prior art

Among Salmonellae causing food poisoning and Salmonellosis infection, important Salmonellae include *S. typhimurium*, *S. typhi*, and *S. enteritidis*, which play a significant role in main food pathogenic bacteria around the world.

Traditionally, the method for detecting *S. typhimurium* comprises steps of pre-culturing, culturing on a selective medium, streak culturing and differentiating on a selective agar medium, biochemical identification of suspected colonies, and serological test, which need a time period of at least 5–7 days that might be too late to be of use for understanding of pathogen in a crisis of food poisoning and salmonellosis infection.

Polymerase chain reaction (PCR) can be rapid and reliable for detecting bacteria and virus in various samples. Among all *Salmonella serovars*, PCR primers useful for detecting *S. typhi* and *S. enteritidis* had been reported in literature, while PCR primers for detecting *S. typhimurium* was rarely seen in literature and patents.

As to the technical level in the state-of-art, related literature and patents can be summarized as follows:

a. Patents associated with the detection of Salmonella: (1) U.S. Pat. No. 5,683,883 (1997) related to PCR primers useful for the detection of all *Salmonella serovars*: (2) U.S. Pat. No. 5,824,795 (1998) related to PCR detections of *S. enteritidis* and *S. bongori*; (3) U.S. Pat. No. 5,714,321 (1998) described nucleotide probes useful for detecting all *Salmonella serovars*; (4) U.S. Pat. No. 5,804,378 (1988) disclosed nucleotide probes useful for detecting related Salmonella genus; (5) U.S. Pat. No. 5,681,716 (1997) related nucleotide sequences useful for the detection of *S. typhi*. As stated above, although there were patents relating DNA probe and PCR methods for detecting Salmonella other than *S. typhimurium*, patent associated with PCR detection of *S. typhimurium* has been rarely seen.

b. Study reports: (1) Olsen et al (1995) reported oligonucleotide probe useful for the detection of Salmonella and *S. typhimurium*, which was designed based on the sequence of a cloned 2.3 Kb DNA fragment, however, this probe was used for detecting DNA-DNA hybridization of *S. typhimurium*; (2) Rahn et al (1992) developed a PCR method for the detection of all *Salmonella serovars*, which method was based on the sequence of invA gene of *S. typhimurium*; (3) Cocolin et al (1998) developed PCR method that could detect 33 serotypes of Salmonella; in combination with hydrolytic analysis by restriction enzyme, *S. typhimurium* could be detected also; (4) Miyamoto et al. (1998) had detected Salmonella including *S. typhimurium* by utilizing RAPD ; (5) Cohen et al. (1996) devised a PCR method based on the sequence of the finA gene of *S. typhimurium* for detecting all *Salmonella serovars* in food samples; (6) Stone et al. (1995) had detected *S. typhimurium* with a PCR-hybridization method that was not a direct PCR detection method; (7) Tuchili et al. (1995) detected chickens infected by *S. gallinarum* or *S. typhimurium* with a PCR method involving the InvA gene, unfortunately, both *Salmonella serovars* were detected; (8) Nastasiru and Mammina(1995) studied the epidemic *S. typhimurium* strains by utilizing a PCR-ribotyping process; (9) Way et al. (1993) detected Salmonella, Shigella, *E. coli*, Citrobacter spp with a multiplex PCR method; (10) in addition, immuno-PCR method had been developed for detecting all serovars Salmonella spp. (Fluit et al 1993; Widjojoatmodjo et al. 1992); (11) Kong et al. (1995) and Chary et al. (1993) reported the detection of *S. typhimurium* in water by using genes of enterotoxin and Aromatase (ARO-A) of *S. typhimurium*, however, its specificity was not further confirmed.

Accordingly, there is a need to provide a method for rapid and specific detection of *S. typhimurium* in food and clinical samples.

SUMMARY OF THE INVENTION

As stated above, one object of the invention is to provide two PCR primers designed based on a DNA sequence of a gene encoding malic acid dehydrogenase and a specific DNA of *Salmonella typhimurium*, respectively.

Another object of the invention is to provide a probe specific for the two primers used in PCR method according to the invention.

Still another object of the invention is to provide a PCR method for the rapid and specific detection of *S. typhimurium* in food and clinical specimens using the two primers and the probe mentioned above.

BRIEF DESCRIPTION OF THE DRAWINGS

The invention, as well as its many advantages, may be further understood by the following detailed description and drawings in which:

FIG. 1 (A) Detection of *S. typhimurium* strains using PCR primers MDH 31 and MDH 2. (B) Southern blot hybridization of the PCR products obtained from (A) with $^{32}$P-labelled probe STM 1. Lane a: 100 bp ladder; lanes b–i: PCR products amplified from 8 *S. typhimurium* strains shown in Table 1. Lane j : negative control with *E. coli* strain E02. Lanes b'–j': Southern blot hybridization results for lanes b~j in FIG. A.

FIG. 3 PCR detection sensitivity for *S. typhimurium* (A) strain ST93 (ATCC 13311) and (B) strain ST94 (ATCC 19585). Experimental conditions were as described in Methods. Lane a: 100 bp ladder; lanes b–h: PCR products amplified from $10^5$–$10^0$ and 0 cfu per assay of *S. typhimurium* strain ST 93 (A) or ST 94 (B).

FIG. 4 Detection of *S. typhimurium* (ATCC 13311) in (A) pasteurized whole milk and (B) raw whole milk after pre-culture with CTET broth for 8 h. Experimental conditions were as described in Methods. Lane a: 100 bp ladder; lanes b–h: PCR products amplified from $10^5$–$10^0$ and 0 cfu target cells per ml of milk.

DETAILED DESCRIPTION OF THE PREFERRED EMBODIMENT

Figure 2:
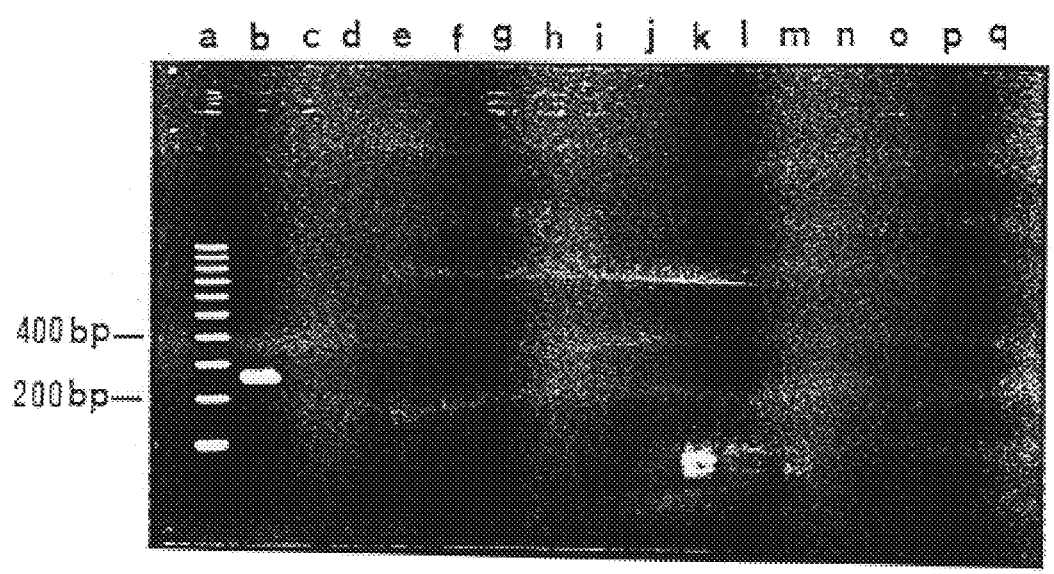
FIG. 2 Detection of Salmonella strains other than *S. typhimurium* using PCR primers MDH 31 and MDH 2. Lane a: 100 bp ladder. Lanes b–q: PCR products amplified from Salmonella strains shown in Table 1, i.e., strains ST 93 (positive control), SA04, 10, 12, 20, 27, 28, 29; SB05, 08, 20, 064; SC14, 15, 16, 25, respectively.

As stated above, one object of the invention is to provide two PCR primers designed based on a DNA sequence of a gene encoding malic acid dehydrogenase essentially involved in Krebs cycle and a specific DNA of *S. typhimurium*, respectively. These two primers are designated as MDH2 and MDH31, respectively, and have DNA sequences as follows:

MDH 31: 5'-TGC CAA CGG AAG TTG AAG TG-3' (SEQ ID: NO:1)

MDH 2: 5'-CGC ATT CCA CCA CGC CCT TC -3' (SEQ ID: NO:2)

Another object of the invention is to provide a probe specific for the two primers used in PCR method according to the invention and has following sequence:

STM 1: 5'-GTC GCA GAT TCC AGG CGT AAG-3' (SEQ ID: NO:3)

Still another object of the invention is to provide a PCR method for the rapid and specific detection of *S. typhimurium* in food and clinical specimens using the two primers and the probe mentioned above. The PCR method comprises steps of incubating the set of primers according to the invention directly with a sample or with an culture amplified from a sample, carrying out PCR under conditions described in Examples and detecting PCR products by Southern blotting assay using the STM1 probe according toa modified Denhardt process (Denhardt, 1966). Wherein, radioactive labeling of the oligonucleotide fragment and the Southern hybridization reaction were performed according to the methods described by Maniatis et al., 1989. the oligonucleotide was 5' labeled with $\gamma$-$^{32}$P-ATP to produce a radioactive probe. DNA hybridization was performed according to a modified Denhardt method (Denhardt, 1966). The temperature of pre-hybridization was 65° C., whereas the temperature of hybridization was 53° C.

The invention will be illustrated further in more detailed in the following non-limiting examples.

EXAMPLES

Bacteria used in examples included 8 *S. typhimurium* strains '45 clinical *S. typhimurium* strains (obtained from National Institute of Preventive Medicine, Department of Health, Executive Yuan, Taipei, Taiwan, R.O.C, ISM1-45), 45 other serovars Salmonella strains, and also 28 enteric and non-enteric bacteria including Bacillus, Citrobacter, Enterobacter, Erwinia, Hafnia, Klebsiella, Kluyvera, Micrococcus, Morganella, Proteus, Serratia, Shigella, Staphylococcus, Vibrio, Yersinia (as listed in Table 1 and 2).

Chemicals used in examples: Ethidium bromide, Sodium dodecyl sulfate (SDS), EDTA, Ficoll, Polyvinylpyrrolidone and Mineral oil were purchased from Sigma (Sigma Chemical Company, St., Louis, Missuouri); 100 bp ladder marker was bought from GenSura (GenSura Laboratories, Inc.); Tris-base, Bovine serum albumin (BSA), dATP, dTTP, dCTP and dGTP were purchased from Boeheringer Mannhein GmbH Biochemia (Postfach, Mannheim, Germany ); T4 polynucleotide kinase was purchased from Bio-Labs (New England Bio Labs, Beverly, Massachusetts); Nylon membrane, $\gamma$-$^{32}$P-ATP, X-ray film (Hyper-film-$\beta$ max) were bought from Amersham (Amersham International Inc., UK); Developer and Fixer were purchased from Kodak; Proteinase K was bought from Merck (Darmstadt, Germany); Sonicated salmon sperm DNA was purchased from Stratagene, UK ; Dynazyme DNA polymerase was bought from FinnzymOy (Riihitontuntie, Finland ); Agarose was a product of Promega (Promega Corporation, Madison, Wisconsin, U. S. A.). All of chemicals mentioned above were reagent grade or analytical grade.

Culturing medium used in examples were as follow:

1. Luria-Bertani broth (LB)
    Yeast extract 5 g
    Tryptone 10 g
    Sodium chloride 10 g
    Distilled water 1000 ml
2. CTET (Combined Tetrathionate) broth
    Lactose broth 13 g
    Sodium thiosulfate 30 g
    Calcium carbonate 10 g
    Bile salt 1 g
    Distilled water 1000 ml heated to boiling and after being cooled to 60° C., Iodine Solution was added (2 ml Iodine Solution per 100 ml broth).

Wherein, Yeast extract, Tryptone, Lactose broth, Bile salt, Peptone and Plate count agar (PCA) were purchased from Difco (Detroit, Mich., U.S.A.); sodium thiosulfate and iodine were bought from Sigma (Sigma Chemical Company, St., Louis, Mo., U.S.A.); and calcium carbonate was bought from A); and calcium carbonate was bought from Wako Pure Chemical Inc. Osaka, Japan.

Dynazyme PCR buffer (10×100 mM Tris-HCl, pH 8.8 at 25° C., 15 mM $MgCl_2$, 500 mM KCl, 1% Triton X-100), T4 polynucleotide kinase buffer used in the invention was supplied by Bio-Labs (New England Bio Labs, Bererly, Mass.). Other buffer solutions and reagents were prepared according to the method described by Maniatis et al (1989). Buffer solution was prepared as follows:

1. 50×TAE buffer
    Tris base 242 g
    Glacial acetic acid 57.1 ml
    0.5 M EDTA (pH8.0) 100 ml
    Water to 1000 ml
2. 6×Loading buffer
    30% (W/V) glycerol
    0.25% (W/V) bromophenol blue
    % (W/V) xylene cyanol
3. 20×SSC buffer
    Sodium chloride 175.3 g
    Trisodium citrate 88.2 g
    Adjusting pH with HCl to 7 and adding water to 1000 ml 4. 100×Denhardt's solution
   Ficoll 2 g
   Polyvinyl pyrrolidone 2 g
   BSA 2 g
   Adding water to 1000 ml and sterile filtering for use
5. The Southern transfer hybridization solution:
   (1) Pre-hybridization solution:
      6×SSC
      10×Denhardt's solution
      0.2% SDS
      Sonicated salmon sperm DNA (200 μg per ml of pre-hybridization solution)
   (2) Hybridization solution:
      6×SSC
      10×Denhardt's solution
      0.2% SDS
      $\gamma$-$^{32}$P-ATP labeled probe (20 pmole per ml of hybridization solution)

PCR thermocycler was Perkin Elmer gene amp PCR system 9600 (Perkin-Elmer Cooperation, Norwalk, Conn., U.S.A.).

Samples to be detected including fresh milk, beef, chicken meat and eggs were obtained from supermarket. Infantile stool to be detected were sampled from hospital.

PCR primers were designed based on the sequence of mdh gene (malate dehydrogenase) that was obtained from biological molecular database GenBank/EMBL/DDBJ via an internet system Gopher. The as obtained sequence data were compared with a multiple sequence format using Wisconsin Sequence Analysis Software Package developed by Genetic Computer Group (GCG) aimed as to find the difference among genes and thereby designed PCR primers specific to S. typhimurium. Primers thus designed were compared with DNA sequences within a biomolecular data bank GenBank/BMBL Release 70.0/27.0 in the Computer Center of the National Chunghsing University via a software FASTA to expel 3' end and other gene pairs.

Oligonucleotide primers used in the invention were commercially synthesized by Perkin Elmer or the Center of Genetic Engineering, National Chunghsing University.

General Procedure of PCR

1. Specificity and sensitivity tests of PCR using primers MDH 2/MDH 31

(1) The specificity: to a 0.5 ml microcentrifuge tube was added 30 μl PCR buffer solution prepared previously (4/3× buffer) following with addition of 10 μl suspension of target or non-target bacteria at about $10^5$ cells per 10 μl. A drop of mineral oil was deposited over the surface of the reaction solution. Thereafter, the centrifuge tube was placed and heated in a PCR thermocycler at 95° C. for 30 minutes to break down bacteria therein. After cooling the temperature to 80° C., 10 μl PCR buffer (1×buffer containing 0.6 unit<Dynazyme DNA polymerase) was added to make a volume of the reaction solution of 50 μl (the final concentration of $Mg^{2+}$ was 1.5 mM). A PCR was carried out using above-mentioned primers (50 pmole/assay in 50 μl) and 200 μM of each dNTP under following reaction conditions: raising the temperature to 94° C. for a thermal initiation reaction for 3 minutes; holding at 94° C. for 20 seconds to split DNA into single strand; lowering the temperature to 67° C. and holding for 30 seconds to bind primers; raising the temperature again to 72° C. to allow an extending polymerization for 30 seconds; running 35 cycles described above; and finally, holding at 72° C. for 5 minutes. The whole process was linked programmatically. For analysis, 10 μl reaction product was sampled, loaded on 3% agarose and performed electrophoresis in 1×TAE buffer. After staining with ethidium bromide, the gel was observed under UV box and then photographed.

(2) The Sensitivity:

After being activated, the bacterial culture was inoculated in 5 ml of LB broth and incubated at 37° C. for 8 hours. Bacterial culture at log phase was serially diluted. 10 μl of S. typhimurium suspension (about $10^5$, $10^4$, $10^3$, $10^2$, $10^1$, $10^0$ cells per 10 μl) and a blank sample were subjected to PCR. PCR and analytical conditions were same as described above.

2. Detection of Milk Products (1) Direct Detection:

After shaking homogeneously, 1 ml of a whole milk or raw milk was PCA counted and then 1 ml each of these was dispensed in centrifuge tubes. 10 μl each of the bacteria culture serially diluted was inoculated (to about $10^6$, $10^5$, $10^4$, $10^3$, $10^2$, $10^1$, $10^0$ CFU per ml milk ) while the blank sample received no bacterial culture. After being centrifuged at 7000×g for 5 minutes, the supernatant was discarded. 1 ml sterile water was added. 10 μl was used directly in PCR, or after adding proteinase K(PK)(Merck, Darmstndt, Germany) (0.3 mg/ml) and reacting at 65° C. for 30 minutes, 10 μl of the resulted solution was used directly in PCR under same conditions and procedures as those described for pure bacteria.

(2) Amplification on CTET Broth:

After shaking homogeneously, 1 ml each of the whole milk or raw milk was added in 9 ml CTET broth contained in a culturing flask. 10 μl each of the bacteria culture serially diluted was inoculated (to about $10^6$, $10^5$, $10^4$, $10^3$, $10^2$, $10^1$, $10^0$ CFU per ml milk ) while the blank sample received no bacterial culture. After being incubated at 37° C. for 8 hours, 100 μl of the incubating mixture was diluted 10-fold with de-ionized water. 10 μl of the dilution was taken for carrying out PCR under same conditions and procedures as those described for pure bacteria.

3. Detection of Target Bacteria in Food (beef, chicken meat and egg)

(1) Direct Detection:

25 g food pieces was mixed with 225 ml of sterile water and beated at high speed with a beater for 2 minutes. 1 ml each of the pulverized food pieces was plate counted. 1 ml was added separately in a centrifuge tube. 10 μl each of the bacteria culture serially diluted was inoculated (to about $10^6$, $10^5$, $10^4$, $10^3$, $10^2$, $10^1$, $10^0$ cell per ml homogenate) while the blank sample received no bacterial culture. After mixing homogeneously, 10 μl was used directly in PCR, or after reacting with PK (0.3 mg/ml) at 65° C. for 30 minutes, 10 μl was used directly in PCR under same conditions and procedures as those described for pure bacteria.

(2) Amplification on CTET Broth:

25 g food pieces was mixed with 225 ml of sterile water and beated at high speed with a beater for 2 minutes. 1 ml each of the pulverized food pieces was plate counted. 100 μl each of the bacteria culture serially diluted was inoculated (to about $10^6$, $10^5$, $10^4$, $10^3$, $10^2$, $10^1$, $10^0$ cell per ml homogenate) while the blank sample received no bacterial culture. After being incubated at 37° C. for 8 hours, 100 μl of the incubating mixture was diluted 10-fold with de-ionized water. 10 μl of the dilution was taken for carrying out PCR under same conditions and procedures as those described for pure bacteria.

3. Detection of Stool Sample

In view of the complexity of stool, two detection manners were employed as described below:

(!) Direct Detection:

With a slightly modified method of Ramotar et al. (1995), 0.1 g~0.5 g of stool was picked up each time with a cotton rod, placed in a small test tube, and diluted with water to a concentration of 0.1 g stool/ml. After shaking homogeneously, 1 ml of the diluted stool mixture was plate counted. 10~50 µl each of the bacteria culture serially diluted was inoculated in other test tubes (to about $10^6$, $10^5$, $10^4$, $10^3$, $10^2$, $10^1$, $10^0$ cells per 0.1 g stools) while the blank sample received no bacterial culture. After shaking homogeneously, 100 µl of the incubating mixture was diluted 10-fold in a micro test tube. 10 µl sterile water was used directly in PCR, or after reacting with PK (0.3 mg/ml) at 65° C. for 30 minutes, 10 µl was used directly in PCR under same conditions and procedures as those described for pure bacteria.

(2) Amplification on CTET Broth:

0.1 g~0.5 g of stool was picked up each time with a cotton rod, placed in a small test tube, and diluted with water to a concentration of 0.1 g stool/ml. After shaking homogeneously, 10~50 µl each of the serially diluted bacteria culture was inoculated in each test tubes (to about $10^6$, $10^5$, $10^4$, $10^3$, $10^2$, $10^1$, $10^0$ cells per 0.1 g stools) the blank sample received no bacterial culture. After shaking homogeneously, 1 ml each was dispensed in 9 ml CTET broth contained in a culturing flask. After being incubated at 37° C. for 8 hours, 100 µl of the incubating mixture was diluted 10-fold with de-ionized water. 10 µl of the dilution was taken for carrying out PCR under same conditions and procedures as those described for pure bacteria.

Example 1

Specificity Against *S. typhimurium* Strains with PCR Detection Using Primers MDH 2/MDH 31.

Upon an PCR amplification against target genes using MDH 2/MDH 31 primers according to the invention at a binding temperature of 67° C., all of the 8 *S. typhimurium* strains produced PCR products having a size as expected (261 bp), as shown in FIG. 1 (A). In order to confirm the reliability of PCR products, Southern DNA hybridization was carried out using a probe STM 1 according to the invention. The results indicated that PCR products from all of the 8 *S. typhimurium* had positive reactions with the STM 1 probe as shown in FIG. 1 (B).

To understand further the detection specificity of PCR using MDH 2/MDH 31 primers, 46 different serovars Salmonella strains other than *S. typhimurium* and other enteric bacteria strains including Shigella, Bacillus, Citrobacter, Yersinia, and *Vibrio parahaemolyticus* were used as test strains in the PCR detection using MDH 2/MDH 31 primers at a binding temperature of 67° C. The results revealed that no interference was seen from these non-*S. typhimurium* strains. Part of the detection result was shown in FIG. 2. Whereas results obtained from strains used in the invention were summarized in Table 1 and 2.

To determine sensitivity of PCR using MDH 31/MDH 2 primers, PCR was carried out at a binding temperature of 67° C. and other conditions (as shown in Table 3). The results revealed that PCR sensitivity against various *S. typhimurium* strains (laboratory designated No. ST 93 and ST 94) under a un-amplified condition was up to $10^0$ CFU per assay, as shown in FIGS. 3(A) and (B). this demonstrated that this set of primers according to the invention exhibited a very good detection sensitivity against pure *S. typhimurium* under a specific combination of test conditions.

Example 2

Detection of Target *S. typhimurium* in Milk Products

*S. typhimurium* was frequently seen in bovines such that its contamination in milk became one of its infection route (McClelland et al., 1994). In view of this, commercial whole milk and raw milk were used as detection samples to study the applicability of PCR detection using primers according to the invention.

Results of direct detection of target bacteria in milk products by PCR using MDH31/MDH2 primers revealed that samples obtained by reconstituting with water after centrifugation of the commercial whole milk and raw milk products yielded sensitivities against of *S. typhimurium* strain ST 93 of $10^0$, $10^3$ CFU/per assay, respectively, that was, $10^2$~$10^5$ CFU per ml sample. Whereas samples obtained by subjecting commercial whole milk and raw milk products to centrifugation and PK treatment yielded those sensitivities against *S. typhimurium* strain ST 93 of $10^0$, $10^2$ CFU/per assay, respectively, that was, $10^2$~$10^4$ CFU per ml sample. In order to increase the detection sensitivity, a selective medium CTET broth (Sveum and Kraft, 1981) was selected to amplify target Salmonella, and then carry out PCR detection on cell lysate.

PCR detection after pre-culturing on CTET broth (37° C., 8–12 hr) demonstrated that whether it was applied on the whole milk or the fresh milk products, the sensitivity against *S. typhimurium* strain ST 93 could be up to $10^0$ CFU/ml milk, as shown in FIGS. 4 (A) and (B).

Example 3

Detection of Target Bacterial in Beef, Chicken Meat and Egg

According to a survey conducted by Centers for Disease Control and Prevention, CDC in 1973 to 1987, 59% of Salmonella infected through food. Teuxe et al. (1991) reported that beef, chicken meat and egg constituted the first, second and third places of food infectious source from Salmonella. Therefore, detection of target bacteria in food products was an object of this example.

Figure 5:
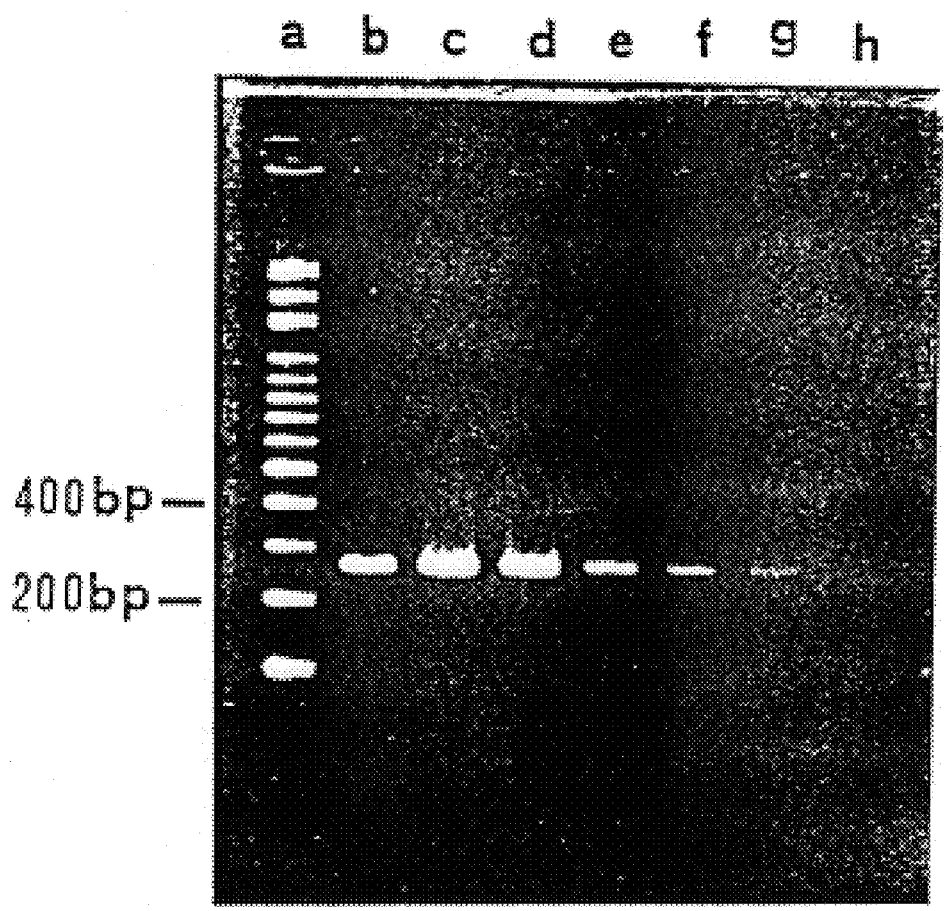
FIG. 5 PCR detection of *S. typhimurium* (ATCC 13311) cells in chicken meat sample after pre-culture with CTET broth for 8 h. Experimental conditions were as described in Methods. Lane a: 100 bp ladder; lanes b–h: PCR products amplified from $10^5$–$10^0$ and 0 cfu target cells per ml of the food homogenate, i.e., per 0.1 g of the food sample.

On the other hand, results obtained through pre-culturing on CTET broth (37° C., 8 hr) and then PCR detecting indicated that, whether applied on beef, chicken meat or egg, sensitivity of this method against *S. typhimurium* strain ST 93 could be up to $10^0$ CFU/ml sample. FIG. 5 shows the PCR detection results on fresh chicken meat.

Example 4

Detection of Infantile Stool

Diarrhea is one of the main symptom of *S. typhimurium* infection (Yang et al., 1989). Therefore, it is essential to apply PCR for the detection of clinical stool specimens. However, the composition of the stool specimens is relatively complex and contains comparatively high content of bacteria (about $10^6$~$10^7$ CFU/0.1 g stools) that might have an extremely effect on the sensitivity and the specificity of the detection. In this example, a method of direct detection with or without the addition of PK, and a detection method after CTET pre-culture were examined.

1. Direct Detection

Figure 6:
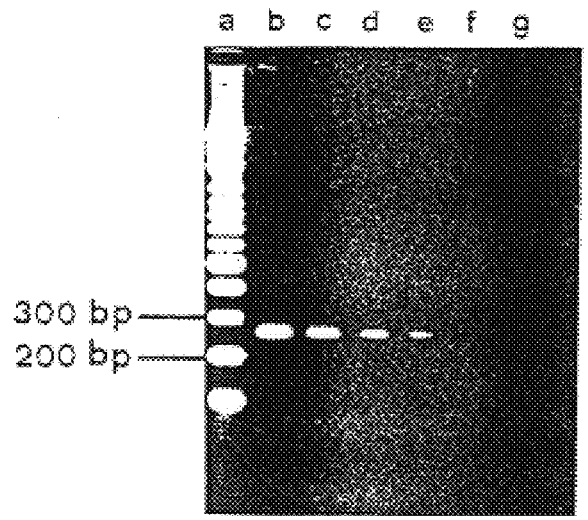
FIG. 6 PCR detection of *S. typhimurium* (ATCC 13311) in human stool specimens. (A) Without pre-culture. (B) After pre-culture of the target cells with CTET broth for 8 h. Experimental conditions were described in Methods. For (A), lane a: 100 bp DNA ladder: lanes b–g: the PCR products amplified from $10^4$–$10^0$ and 0 (blank) cfu of target cells per assay, i.e., $10^7$–$10^3$ and 0 cfu of the target cells per 0.1 g of the stool specimen. For (B); lane a: 100 bp DNA ladder; lanes b–h: PCR products amplified from $10^5$–$10^0$ and 0 (blank) cfu target cells per 0.1 g of stool specimen.
Figure 6:
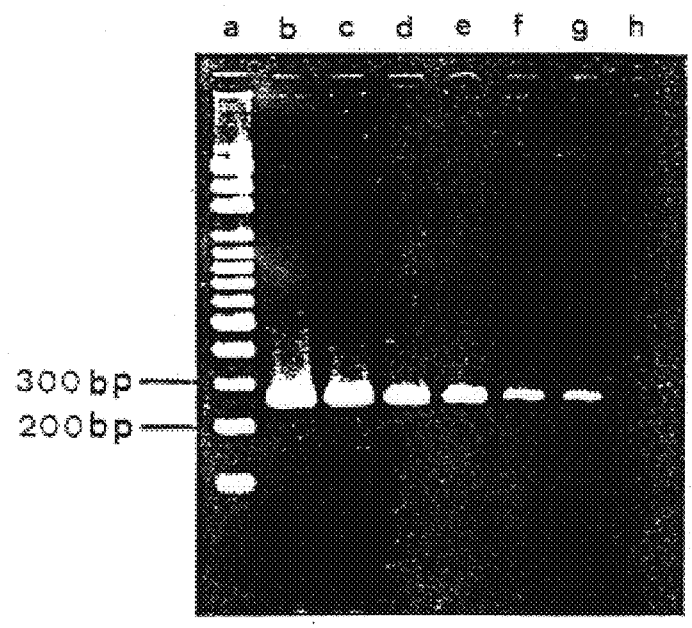

Stool specimens were diluted with sterile water to a concentration of 0.1 g stool/ml. Bacterial with different dilution were inoculated, boiled and carried out PCR. The results indicated that, in the presence or absence of PK, PCR detection using MDH 31/MDH 2 primers could achieve a sensitivity up to $10^0$ CFU /assay, that was, $10^3$~$10^4$ CFU/ 0.1g stool sample, as shown in FIG. 6A.

Amplification on CTET Broth

Stools specimens containing serially diluted bacteria suspension were diluted separately into 1 ml stool suspension.

9 ml each of a selective medium, CTET broth was added and, after performing an pre-culture for amplification over 8–12 hours, PCR detection was carried out. The results indicated that the sensitivity of PCR detection using MDH 31/MDH 2 primers could achieve $10^0$ CFU/0.1 g stool, while the blank specimen without adding bacteria suspension yielded no product, as shown in FIG. 6B. it is surprisingly that $10^0$ CFU of S. typhimurium target strain in the presence of $10^7$ CFU of contaminated bacteria could be detected after a pre-culturing process on a selective medium. It was postulated that this was resulted from an advantageously competitive growth of the target bacterial on the selective CTET broth medium over contaminated bacteria in the infantile stools such that an at least $10^4$-fold increased growth of the expected bacteria could be achieved, as well as in combination with the extremely high sensitivity of PCR using MDH 31/MDH 2 primers.

Many changes and modifications in the above-described embodiment of the invention can, of course, be carried out without departing from the scope thereof. Accordingly, to promote the progress in science and the useful arts, the invention is disclosed and is intended to be limited only by the scope of the appended claims.

References

1. China National Standards (CNS): Method of Test for Food Microbiology-Test of Salmonella. CNS No. 10952, Class No. N6212, Taipei, Taiwan.
2. Department of Health, Executive Yuan, Taipei (1987) Manual for Test of Food Sanitation, Department of Health, Executive Yuan, Taipei, Taiwan.
3. Wang, T. K., Tseng, T. C., Lee, J. H., Wang, W. T., Tsai, j.l., Ho, S. I. And Pan, T. M. 1994. Analysis of *Salmonella serovars* in Taiwan by the phase induction method. Chinese J. Microbiol. Immunol. (Taipei) 27:13–24.
4. Department of Health, Executive Yuan, Taipei, (1997). Survey of Food-borne Outbreaks in 1997 in Taiwan. Department of Health, Executive Yuan, Taipei, Taiwan.
5. Aabo, A., O. F. Rasmussen, L. Rossen, P. D. Sorensen and J. E. Olsen. 1993. Salmonella identification by polymerase chain reaction. Molecular and Cellular Probes. 7: 171–178.
6. Bej, A. K., M. H. Mahbabani, M. J. Boyce and R. M. Atlas. 1994. Detection of Salmonella spp. in ogster by PCR. Applied and Environmental Microbiology 60:368–373.
7. Chary P., R. Prasad, A. K. Chopra and J. W. Peterson. 1993. Location of the enterotoxin gene from *Salmonella typhimurium* and characterization of the gene products. FEMS Microbiol. Lett. 111:89–92.
8. Cocolin, L., M. Manzano, C. Cantoni, G. Comi. 1998. Use of PCR and restric enzyme analysis to directly detect and identify *Salm. typhimurium* in food, J. Appl. Micro. 85: 673–677.
9. Cohen, H. J., S. M. Mechanda and W. Lin. 1996. PCR Amplification of the filmA Gene Sequence of *Salmonella typhimurium*, a Specific Method for Detection of Salmonella spp. Applied and Environmental Microbiology. 62(12): 4303–4308.
10. Denhardt, D. T. 1966. A membrane-filter tenichque for detection of complementary DNA. Biochem. Biophys. Res. Commun. 23: 641–646.
11. Food and Drug Administration 1995. Bacteriological Analytical Manual, $8^{th}$ edition. Arlington, Va., USA, Association of Analytical Chemists.
12. Hashimoto, Y., Y. Itho, Y. Fujinaga, A. Q. Khan, F. Sultana, M. Miyake, K. Hirose, H. Yamamoto and T. Ezaki. 1995. Development of Nested PCR Based on the ViaB Sequence To Detect *Salmonella typhi*. J. Clin. Microbiol. 33 (3): 775–777.
13. Jones, D. D., R. Law and A. K. Bej, (1993) Detection of Salmonella spp. in oysters using polymerase chain reactions (PCR) and gene probes. Journal of Food Science. 58:1191–1197.
14. Kang, R. Y. C., W. F. Dung; L. Lp. RIJMOED, and R. S. S. Wu, 1995. Co-detection of three species of waterborne bacteria by multiplex PCR. Marine Pollut. Bull. 31:317–321.
15. Lampel, K. A., S. P. Keasler and D. E. Hanes. 1996. Specific detection of *Salmonella enterica* serotype Enteritidis using the polymerase chain reaction. Epidemiol. Infect. 116: 137–145.
16. Lin, C. K. and H. Y. Tsen. 1996. Use of two 16S DNA targeted oligonucleotides as PCR primers for the specific detection of Salmonella in foods. Journal of Applied Bacteriology. 80: 659–666.
17. Maniatis, T., C. J. Fritsch and J. Sambrook. 1989. Molecular cloning: a Laboratory manual. Cold Spring Harbor Laboratory, Cold Spring Harbor, N.Y.
18. McClelland, R. G. and A. C. Pinder. 1994. Detection of *Salmonella typhimurium* in dairy products with flow cytometry and monoclonal antibodies. Appl. Environ. Microbiol. 60: 4255–4252.
19. Millemann, Y., M. C. Losage, E. chaslus-Dancla and J. P. Lafont 1995. Value of plasmid profiling, ribotyping and detection of IS2000 for tracing avian isolates of *Salmonella typhimurium* and *S. enteritidis*. Journal of Clinical Microbiology. 33:173–179.
20. Miyamoto, T. Tian HZ., Okabe T, Trevanid S, Asoh K, Tomoda S, Honjoh K, Hatano S, 1998. Application of RAPD for detection of Salmonella spp. in foods. J. Food Prot. 61:785–791.
21. Nastasi A, Mammina C. 1995. Epidemiological evaluation by PCR ribotyping of sporadic and out-break associated strains of Salmonella enterica serotype Typhimurium. 146:99–106.
22. Olesen, J. E., S. Aabo, C. F. Rasmussen and L. Rossen. 1995. Oligonucleotide probes specific for the genus Salmonella and for *Salm. Typhimurium*. Letters in Applied Microbiology. 20: 160–163.
23. Rahn, K., De Grandis S A, Clarke R C, McEwen S A, Galan J E, Giuocchioc, Curtiss R. 3d, Gyles CL. 1992. Mol. Cell. Probe. 6:271–279
24. Ramotor, K., B. Waldhart, D. Church, R. Szumski and T. J. Louie. 1995. Direct Detection of Verotoxin-Producing *Escherichia coli* in Stool Samples by PCR. 1995. J. Clin. Microbiol. 33 (3): 519–524.
25. Schmidt, H., C. Knop, S. Franke, S. Aleksic, J. Heesemann and H. Karch. 1995. Development of PCR for Screening of Enteroaggregative *Escherichia coli*. J. Clin. Microbiol. 33 (3): 701–705.
26. Stacy-Phipps, S., J. J. Mecca and J. B. Weiss. 1995. Multiplex PCR Assay and Simple Preparation Method for Stool Specumens Detect Enterotoxigenic *Escherichia coli* DNA during Course of Infection. J. Clin. Microbiol. 33 (5): 1054–1059.
27. Schraft, H., and M. W. Griffiths. 1995. Specific oligonucleotide primers for detection of lecithinase-positive Bacillus spp. by PCR. Appl. Environ. Microbiol. 61: 98–102.
28. Stone G G. Et al. 1995. Detection of *Salmonella typhimurium* from rectal swabs of experinmentally infected beagles by short cultivation and PCR-hybridization. J. Clin. Microbiol. 33:1292–1295.

29. Song, J. H., H. Cho, M. Y. Park, D. S. Na, H. B. Moon and C. H. Pai. 1993. Detection of *Salmonella typhi* in the blood of patients with typhoid fever by polymersae chain reaction. J. Clin. Microbiol. 31: 1439–1443.
30. Sveum, W. H and A. A. Kraft. 1981. Recovery of Salmonellae from Foods using a Combined Enrichment Technique. Journal of Food Science. 46: 94–99.
31. Teuxe, R. V. 1991. Salmonella, a postmodern pathogen. Journal of Food Protection. 54: 563–568.
32. Tsen, H. Y, and T. R. Chen. 1992. Use of polymerase chain reaction for specific detection of type A, D, and E enterotoxigenic *Staphylococcus aureus* in foods. Appl. Microbiol. Biotech. 37: 685–690.
33. Tsen, H. Y., T. R. Chen and G. K. Yu. 1994. Detection of B and C types enterotoxigenic *Staphylococcus aureus* using polymerase chain reaction. J. Chinese Agric. Chem. Sci. 32(3): 322–331.
34. Tsen, H. Y., W. R. Chi and C. K. Lin. 1996. Use of Novel Polymerase Chain Reation Primers for the Specific Detection of Heat-Labile Toxin I, Heat-Stable Toxin I and II Enterotoxigenic *Escherichia coli* in Milk. J. F. Protect. 59 (8): 795–802.
35. Tsen, H. Y., and L. Z. Jian. 1998. Development and use of a multiplex PCR system for the rapid screening of heat labile toxin I, heat stable toxin II and shiga-like toxin I and II genes of *Escherichia coli* in water. J. Appl. Microbial. 84: 585–592.
36. Tsen, H. Y., J. W. Liou and C. K. Lin. 1994. Possible Use of a Polymerase Chain Reaction Method for Specific Detection of Salmonella in Beef. Journal of Fermentation and Bioengineering. 77(2): 137–143.
37. Tuchili, L. M., Kodama, H., Izumoto, Y, Mukamoto, M., Fukata, T. and Baba, T. (1995) Detection of *Salmonella gallinarum* and *S. typhimurium* DNA in experimentally infected chicks by PCR. J. Det. Med, Sci. 57:59–63.
38. U.S. Pat. No. 5,683,883. Ohashi et al. (1997) Oligonucleotides for detecting Salmonella species and detection process using the same.
39. U.S. Pat. No. 5,824,795. Popoff et al. (1998) Oligonuclotide for the detection of Salmonella.
40. U.S. Pat. No. 5,714,32. Hogan, J. J. (1998) Nucleic acid sequences derived from the genome of *Salmonella typhi* and their uses, in particular for the in vitro diagnosis of the presence of bacteria of the Salmonella genus in food stuff.
41. U.S. Pat. No. 5,681,716. Popoff et al. (1997) Nucleic acid sequences from *Salmonella typhi* for in vitro diagnosis in food stuff.
42. Victor, T., R. D. Toit, J. van Zyl, A. J. Beslir and P. D. van Helden. 1991. Improved method for the routine identification of toxigenic *Escherichia coli* by DNA amplification of a conserved region of the heat-labile toxin A subunit, J. Clin. Microbiol. 29: 158–161.
43. Way, J. S., K. L. Josephson, S. D. Pillai, M. Abbaszadegan, C. P. Gerba and I. L. Pepper. 1993. Specific Detection of Salmonella spp. by Multiplex Polymerase Chain Reaction. Applied and Environmental Microbiology. 59(5): 1473–1479.
44. Xiong, H., Y. Li, M. F. Slavik, and J. T. Walker (1998) Spraying chicken skin with selected chemicals to reduce attached *Salmonella typhimurium*. Journal of Food Protection. 61:272–275.
45. Yang, M. K and M. S. Tan. 1989. Characterization and Cloning of Enterotoxin Genes of *Salmonella typhimurium*. Proc. Natl. Sci. Counc. 13(2): 109–118.
46. Zhu, Q., C. K. Lim and Y. N. Chan. 1996. Detection of *Salmonella typhi* by polymerase chain reaction. Journal of Applied Bacteriology. 80: 244–251.

TABLE 1

*Salmonella typhimurium* strains and other *Salmonella spp.* strains used in this study, and their specificity to PCR primers MDH31/MDH2.

| Lab. No. Strains | Source | Species | PCR |
|---|---|---|---|
| ST 61 | PT | *Salmonella typhimurium* | + |
| ST 62 | USDA 1024 | *S. typhimurium* | + |
| ST 70 | ATCC 14028 | *S. typhimurium* | + |
| ST 80 | ATCC e23566 | *S. typhimurium* | + |
| ST 91 | | *S. typhimurium* | + |
| ST 92 | | *S. typhimurium* | + |
| ST 93 | ATCC 13311 | *S. typhimurium* | + |
| ST 94 | ATCC 19585 | *S. typhimurium* | + |
| ISM[a] (45 strains) | Clinical samples | *S. typhimurium* | + |
| SA 04 | US | *S. aberdeen* | − |
| SA 10 | PT 624 | *S. agona* | − |
| SA 12 | USDA | *S. alachua* | − |
| SA 20 | PT | *S. anatum* | − |
| SA 27 | US | *S. allandale* | − |
| SA 28 | USDA, TUF 18673A | *S. arkansas* | − |
| SA 29 | US | *S. arkansas* | − |
| SB 05 | TUF5429E | *S. bietri* | − |
| SB 064 | USDA1284E | *S. berta* | − |
| SB 08 | US | *S. boecker* | − |
| SB 20 | PT 643 | *S. bousso* | − |
| SC 14 | USDA671D | *S. cerro* | − |
| SC 15 | USDA | *S. cerro* | − |
| SC 16 | TUF18703E | *S. cerro* | − |
| SC 25 | US | *S. chittagong* | − |
| SC 70 | US | *S. crossness* | − |
| SD 30 | US | *S. djakarta* | − |
| SD 41 | USDA1146B1 | *S. dublin* | − |
| SD 50 | US | *S. dugbe* | − |
| SE 05 | ATCC13076 | *S. enteritidis* | − |
| SF 10 | USDA | *S. florida* | − |
| SF 20 | US | *S. florida* | − |
| SG 10 | PT | *S. gallinarum* | − |
| SG 15 | USDA1306DB | *S. gera* | − |
| SH 011 | TUF6503D | *S. haardt* | − |
| SH 18 | US | *S. havana* | − |
| SH 30 | USDA | *S. hvittingfoss* | − |
| SH 40 | US | *S. hvittingfoss* | − |
| SI 001 | TUF 9033C | *S. illinois* | − |
| SJ 08 | US | *S. javiana* | − |
| SM 03 | USDA1306A | *S. mehaden* | − |
| SM 141 | TUF 7908B | *S. minnesota* | − |
| SM 15 | USDA | *S. miami* | − |
| SM 20 | PT625 | *S. muenchen* | − |
| SN 30 | PT695-1 | *S. ngor* | − |
| SP 10 | PT158 | *S. panama* | − |
| SP 15 | US | *S. panama* | − |
| SP 20 | PT398 | *S. paratyphi* A | − |
| SP 30 | PT663 | *S. paratyphi* B | − |
| SP 35 | USDA | *S. pomona* | − |
| SP 37 | USDA | *S. poona* | − |
| SS 28 | USDA1073AM | *S. senftenberg* | − |
| SS 30 | PT169 | *S. senftenberg* | − |
| ST 05 | USDA1221D | *S. tasksony* | − |
| ST 23 | USDA1101E | *S. thomasville* | − |
| ST 51 | ATCC8427 | *S. typhi* | − |

ATCC : American Type Culture Collection, Maryland, U.S.A.
PT : National Ping Tung College of Technologies, R.O.C.
US : The City of New York Department of Health, U.S.A.
USDA : United State Department of Agriculure.
[a]ISM : Strains of *S. typhimurium* from. National Institute of Preventive Medicine, Department of Health, Executive Yuan, Taipei, Taiwan, R.O.C

TABLE 2

Non-*Salmonella spp.* bacteria strains used in this study, and their specificity to PCR primers MDH31/MDH2.

| Lab. No. Strains | Source | Species | PCR |
|---|---|---|---|
| BAC 10 | CCRC10446 (ATCC11778) | *Bacillus cereus* | − |
| BC3 | CCRC10603 (ATCC14579) | *Bacillus cereus* | − |
| BRE 10 | ATCC 19391 | *Brevibacterium linens* | − |
| CIT 20 | CCRC10041 (ATCC 8090) | *Citrobacter cloacae* | − |
| E 02 | ATCC 25922 | *Eschrichia coli* | − |
| ETEC 01 | ATCC 35401 | Enterotoxigenic *E. coli* | − |
| EPEC 02 | CVD | Enteropathogenic *E. coli* | − |
| EHEC 06 | | Enterohemorrhagic *E. coli* | − |
| EIEC 01 | CVD | Enteroinvasive *E. coli* | − |
| EaggEC 01 | CVD | Enteroaggregative *E. coli* | − |
| CIT 30 | FR 12291 | *Citrobacter freundii* | − |
| ENT 20 | US (ATCC 23355) | *Enterobacter cloacae* | − |
| ERW 10 | CCRC 11298 | *Erwinia carotovora* | − |
| HAF 10 | CCRC 10906 (ATCC 9890) | *Hafnia alvei* | − |
| KLE 20 | US | *Klebiells pneunoniae* | − |
| KLU 10 | CCRC 11645 (ATCC14236) | *Kluyvera ascorbata* | − |
| MIC 10 | CCRC 11577 (ATCC 9815) | *Micrococcus roseus* | − |
| MOR 10 | CCRC 10706 (ATCC25830) | *Morganella morganii* | − |
| PRO 10 | ATCC 8427 | *Proteus vulgaris* | − |
| PSE 20 | FR 10735 | *Pseudomonas cepacia* | − |
| SER 10 | ATCC 13880 | *Serratia marcesens* | − |
| SHI 10 | CCRC 10772 (ATCC12022) | *Shigella flexneri* | − |
| SHI 11 | CCRC 13894 (ATCC29903) | *Shi. flexner* | − |
| SHI 20 | CCRC 10773 (ATCC9290) | *Shi. sonnei* | − |
| SHI 21 | CCRC 10774 (ATCC11060) | *Shi. sonnei* | − |
| SHI 30 | CCRC 15959 (ATCC 8700) | *Shi. boydii* | − |
| SHI 40 | CCRC 13893 (ATCC13313) | *Shi. dysenteria* | − |
| VP 01 | ATCC 17803 | *Vibrio. parahaemolyticus* | − |

ATCC : American Type Culture Collection, Maryland, U.S.A.
CVD : Center for Vaccine Development, University of Maryland School of Medicine, Baltimore ; CVD.
CCRC : Culture Collection and Research Center, Taiwan
US : The City of New York Department of Health, U.S.A.

What is claimed is:

1. A PCR primer composition that specifically amplifies of a 261 base pair DNA of *Salmonella typhimurium*, said composition comprising compounds MD31 and MDH2 wherein the compound MD31 consists of SEQ ID NO:1 and the compound MDH2 consists of SEQ ID NO:2.

2. A DNA probe which specifically hybridizes to a 261 base pair *Salmonella typhimurium* amplification product, wherein said 261 base pair *Salmonella typhimurium* amplification product is obtained by specifically amplifying *Salmonella typhimurium* nucleic acids by PCR using compounds MD31 and MDH2 as primers; wherein the compound MD31 consists of SEQ ID NO:1 and the compound MDH2 consists of SEQ ID NO:2; and wherein said DNA probe is compound STM1 which consists of SEQ ID NO:3.

3. A method for detecting *Salmonella typhimurium* in a sample which comprises incubating said sample with primers MD31 and MDH2 in a PCR reaction solution whereby a PCR reaction takes place which amplifies *Salmonella typhimurium* nucleic acids to produce a 261 base pair *Salmonella typhimurium* amplification product; and then detecting the presence of said 261 base pair *Salmonella typhimurium* amplificatio product by Southern hybridization using a probe, wherein the presence of said amplification product is indicative of the presence of *Salmonella typhimurium* in the sample; said probe being compound STM1 which consists of SEQ ID NO:3; said primer MD31 being a compound which consists of SEQ ID NO:1 and said primer MDH2 being a compound which consists of SEQ ID NO:2.

* * * * *